United States Patent [19]

Hufford et al.

[11] Patent Number: 4,873,250

[45] Date of Patent: Oct. 10, 1989

[54] ANTIMICROBIAL COMPOUND AND COMPOSITIONS PARTICULARY EFFECTIVE AGAINST CANDIDA ALBICANS

[75] Inventors: Charles D. Hufford; Alice M. Clark, both of Oxford, Miss.

[73] Assignee: The University of Mississippi, University, Miss.

[21] Appl. No.: 218,993

[22] Filed: Jul. 14, 1988

[51] Int. Cl.$^4$ .................... C07D 471/00; A61K 31/44
[52] U.S. Cl. ...................................... 514/290; 546/111
[58] Field of Search ......................... 546/111; 514/290

[56] References Cited

PUBLICATIONS

De Almeida et al., Chem. Abstracts, vol. 85(25), abst. no. 85:192943-j, Dec. 20, 1976.
Koyama et al., Heterocycles, vol. 12(8), pp. 1017–1019, Aug. 1, 1979.

*Primary Examiner*—Alan L. Rotman
*Attorney, Agent, or Firm*—William D. Stokes

[57] ABSTRACT

The use of the naturally occurring and readily synthesized alkaloid compound onychine as an antimicrobial agent and particularly against *Candida albicans* organism.

3 Claims, No Drawings

ANTIMICROBIAL COMPOUND AND COMPOSITIONS PARTICULARY EFFECTIVE AGAINST CANDIDA ALBICANS

FIELD OF THE INVENTION

This invention is directed to the new antimicrobial, onychine, compositions thereof and a method of providing effective protection against pathological conditions in mammals particularly those caused by *Candida albicans*. The compound and compositions of the invention provide a simple, practical drug which may be effectively administered alone or in admixture with known non-toxic pharmaceutically-acceptable diluent carriers. The compound may be simply and practically synthesized relatively inexpensively.

SUMMARY AND BACKGROUND OF THE INVENTION

*Candida albicans* is a pathogenic yeast fungus which can cause severe and resistant to treatment infections in mammals, for example, moniliasis of the mouth. Infections (candidiasis) caused by *Candida albicans*, are extremely resistant to treatment but, under normal conditions, rarely fatal. On the other hand, *Candida albicans* is an opportunistic and dangerous organism should it infect persons having comprised immune systems such as, for example, AIDS patients and cancer patients undergoing chemotherapy. Under such circumstances, an infection by *Candida albicans* can become quite fatal. Prior to this invention, the principal and, substantially only, treatment of choice for *Candida albicans* has been the drug amphotericin-B. As well known in the art, treatment with amphotericin-B has a great many disadvantages causing numerous and, quite serious, adverse side effects. In humans, the side effects include, under varying conditions, fever, anorexia, nausea and vomiting, diarrhea, muscle and joint pain, phlebitis and thiophlebitis, anemia, abnormal renal function, anuria, cardiovascular distress, hypertension and hypotension.

There has been a continuing search and extensive efforts made to discover a new and clinically useful agent against *Candida albicans* which may be used as an alternative to amphotericin-B. In accordance with the invention, it has been discovered that the compound onychine, and therapeutic compositions comprising onychine, has remarkable anticandidal activity.

The discovery and extraction of eupolauridine from the tree found throughout West Africa, and its possibly remarkable anticandidal properties, was reported in the Journal of Natural Products, Vol. 50, No. 5, pp. 961-964, Sept.-Oct. 1987, by Hufford, Shihchih Liu, Clark and Babajide Oguntimein.

During the synthesis of eupolauridine, the intermediate compound onychine was discovered to be an effective treatment against *Candida albicans*. Treatment against *Candida albicans* utilizing the drug of the invention may be by any of the conventional routes of administration, for example, oral, intramuscular, intravenous, or rectally. Onychine is preferably administered in combination with a pharmaceutically-acceptable carrier which may be solid or liquid, dependent upon choice and route of administration. Examples of acceptable carriers include, but are not limited to, starch, dextrose, sucrose, lactose, gelatin, agar, stearic acid, magnesium stearate, acacia, and similar carriers. Examples of liquids include water, edible oils, e.g. peanut and corn.

When administered in solid form, onychine and a diluent carrier may be in the form of tablets, capsules, powders, lozenges, suppositories prepared by any of the well known methods. When given as a liquid preparation, the mixture of active compound and liquid diluent carrier may be in the form of a suspension administered as such. Onychine is administered in a non-toxic dosage concentration sufficient to inhibit the growth and/or destroy the *Candida albicans* organism. The actual dosage unit will be determined by such generally recognized factors as body weight of the patient and/or severity and type of pathological condition the patient might be suffering with prior to becoming infected with the *Candida albicans* organism. With these considerations in mind, the dosage of a particular patient can be readily determined by the medical practitioner in accordance with the techniques known in the medical arts.

DETAILED DESCRIPTION OF THE INVENTION

Onychine has the structural formula:

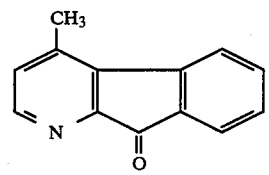

The onychine compound of the invention was simply and readily prepared by the method of Bowden et al., Aust. J. Chem., 28, 2681 (1975). Following the published procedure onychine was prepared as follows:

To a stirred, cooled (0°) solution of ethyl benzoylacetate (200 g) and concentrated ammonia in ethanol (1 L) was added crotonaldehyde (110 g) at a rate 2.5 ml/min while the temperature was kept below 10°. The mixture was warmed to room temperature overnight and concentrated in vacuo to give a yellow oily residue (260 g). The residue was treated with a mixture of con $H_2SO_4$ (100 ml), con $HNO_3$ (130 ml) and water (580 ml) and the mixture cautiously heated on a steam bath until the evolution of $NO_2$ had subsided, then heated for another 30 min. After cooling, the supernatant was basified with con $NH_4OH$ and extracted with diethyl ether (300 ml×10). The combined ether extracts were concentrated to leave a dark brown oily residue (38 g). Purification of the residue by silica gel column chromatography (70 - 230 mesh, 400 g, 42×5 cm, three times) using n-hexaneethyl acetate (2:1) as eluent afforded 15 g of ethyl-4-methyl-2-phenylnicotinate. Hydrolysis of ethyl-4-methyl-2-phenylnicotinate (15 g) with refluxing ethanolic KOH, followed by work-up afforded 4-methyl-2-phenylnicotinic acid (9 g) as colorless prisms, mp 210°-212°. Treatment of 4-methyl-2-phenylnicotinic acid (9 g) with polyphosphoric acid (166.7 g) at 130° for 3 hr., afforded 1-methyl-4-azafluoren-9-one, onychine, (7.5 g) as yellow prisms from n-hexane, mp 130°-131° C.

Onychine, prepared as described above, was discovered to exhibit a remarkable zone of inhibition against three test strains of *Candida albicans*. The minimum inhibitory concentration (MIC) of onychine was found to be 3.12 μg/ml for *Candida albicans* B311 in yeast-nitrogen broth.

In vitro evaluation of the anticandidal activity of the inventive compound and compositions was carried out using the agar-well diffusion assay as follows:

*Candida albicans* NIH B311 used to induce experimental disseminated candidiasis was used for the initial qualitative evaluation of anticandidal activity. The organism was grown in Sabouraud-dextrose broth (SDB) for 14 hours at 37°, at which time the cells were harvested by centrifugation (4°, 2000 rpm, 3 min). After centrifugation, the cells were washed and suspended in sterile 0.9% saline to give a final concentration of $10^6$ colony forming units (CFU) per ml (adjusted using a hemocytometer). Culture plates (15×100 mm) for the qualitative assay were prepared from 25 ml of Sabouraud-dextrose agar. Using sterile cotton swabs, the plates were streaked with the suspension ($10^6$ CFU/ml) of *Candida albicans* B311. Cylindrical plugs were removed from the agar plates by means of a sterile cork borer to produce wells with a diameter of approximately 11 mm. To the well was added 100 μl of solution or suspension of an extract, fraction, or pure compound. Crude extracts and fractions were tested at a concentration of 20 mg/ml, whereas pure compounds were tested at 1 mg/ml. When solvents other than $H_2O$, EtOH, MeOH, DMSO, DMF, or $Me_2CO$ were required to dissolve extracts or compounds, solvent blanks were included. Anticandidal activity was recorded as the width (in mm) of the zone of inhibition following incubation of the plates at 37° for 24 hours. The antifungal agents amphotericin-B and ketoconazole were included as standards in each assay.

The method used to determine the minimum inhibitory concentration (MIC) of the inventive compound was a twofold serial broth dilution assay in yeast nitrogen broth. In addition to *Candida albicans* B311, the MIC values for onychine were also determined for two additional strains of *Candida albicans*: ATCC 10231 and a clinical isolate, designated WH. Also tested were *Mycobacterium smegmatis* 607, *Bacillus subtilis*, 6633, *Cryptococcus neoformans* 32264, *Aspergillus flavus* 9170, *Aspergillus fumigatus* 26934, and *Trichophyton mentagrophytes* 9972. The inventive compound was initally tested using a concentration of 100 μg/ml in the first tube. The compound was added to sterile Sabourauddextrose broth as a solution in DMSO. The inoculum for the MIC determination was prepared as described for qualitative evaluation. Using a calibrated sterile wire loop, 10μl of the $10^6$ CFU/ml suspension of *Candida albicans* was used as inoculum for each tube. The MIC value was taken as the lowest concentration of compound that inhibited the growth of the test organisms after 24 and 48 hours of incubation at 37°. The antifungal agents amphotericin-B and ketoconazole were included as standards in each screen.

The results of the MIC testing for various pathogenic agents is set out in Table I.

TABLE I

| Organism | MIC μg/ml Onychine |
|---|---|
| *Candida albicans* B311 | 3.12 |
| *Candida albicans* 10231 | 1.56 |
| *Candida albicans* WH | 25 |
| *Cryptococcus neoformans* 32264 | |
| *Aspergillus flavus* 9170 | |
| *Aspergillus fumigatus* 26934 | |
| *Trichophyton mentagrophytes* 9972 | |

In the in vivo testing of the invention onychine, outbred mice were used. A disseminated infection of *Candida albicans* in the test animals was achieved by intravenous injection of $10^6$ CFU of the pathogen. The organism is rapidly cleared from the blood and most tissues, except the kidney which is the primary target organ for the disseminated infection in mice. It is known than an inoculum of $10^6$ CFU will produce a disseminated infection in outbred mice within 2-4 hours. Onychine was administered to infected mice by intraperitoneal injection 7 hrs post-inoculation. The vehicle used for administering the compound of the invention was a mixture consisting of 50% USP water, 40% propylene glycol and 10% absolute ethonol. The results of the in vivo tests are set out in Table II. The number of CFU of *Candida albicans* recovered from the kidneys of mice treated with 0.1 mg onychine/kg of body weight were significantly lower than the number of CFU of *Candida albicans* recovered from vehicle treated control mice. Thus, onychine, at a dose of 0.1 mg/kg was capable of significantly reducing the number of *Candida albicans* in the kidney.

TABLE II

| Onychine, mg/kg (n) | CFU/g × $10^6$ (range) | P | % Reduction |
|---|---|---|---|
| Vehicle Control (7) | 3.75 (0.16-2.01) | | |
| 0.5 (7) | 0.50 (0.11-1.05) | 0.082 | 86.7 |
| 0.1 (8) | 0.17 (0.05-0.3) | 0.047 | 95.5 |

The invention has been described in detail with particular reference to the preferred embodiments thereof; however, it is to be understood that modifications may be made without departing from the spirit and scope of the invention.

We claim:

1. An antimicrobial composition consisting essentially of onychine in a therapeutically-effective concentration and a non-toxic, pharmaceutically-acceptable carrier.

2. A method for preventing pathological conditions in mammals brought about by the presence of *Candida albicans* organism comprising administering to said mammals in a therapeutically-effective concentration, a composition consisting essentially of onychine and a non-toxic, pharmaceutically-acceptable carrier.

3. A composition effective against *Candida albicans* consisting essentially of onychine in a therapeutically-effective concentration and a non-toxic, pharmaceutically-acceptable carrier.

* * * * *